US011568080B2

(12) United States Patent
Stankiewicz et al.

(10) Patent No.: US 11,568,080 B2
(45) Date of Patent: Jan. 31, 2023

(54) SYSTEMS AND METHOD FOR OBFUSCATING DATA USING DICTIONARY

(71) Applicant: 3M INNOVATIVE PROPERTIES COMPANY, St. Paul, MN (US)

(72) Inventors: Brian J. Stankiewicz, Mahtomedi, MN (US); Eric C. Lobner, Woodbury, MN (US); Richard H. Wolniewicz, Longmont, CO (US); William L. Schofield, Silver Spring, MD (US)

(73) Assignee: 3M Innovative Properties Company, St. Paul, MN (US)

( * ) Notice: Subject to any disclaimer, the term of this patent is extended or adjusted under 35 U.S.C. 154(b) by 378 days.

(21) Appl. No.: 15/036,537

(22) PCT Filed: Nov. 10, 2014

(86) PCT No.: PCT/US2014/064741
§ 371 (c)(1),
(2) Date: May 13, 2016

(87) PCT Pub. No.: WO2015/073349
PCT Pub. Date: May 21, 2015

(65) Prior Publication Data
US 2016/0300075 A1 Oct. 13, 2016

Related U.S. Application Data

(60) Provisional application No. 61/904,223, filed on Nov. 14, 2013.

(51) Int. Cl.
*G06F 21/62* (2013.01)
*G06F 16/2455* (2019.01)
*G16H 50/70* (2018.01)

(52) U.S. Cl.
CPC .... *G06F 21/6245* (2013.01); *G06F 16/24568* (2019.01); *G16H 50/70* (2018.01); *G06F 2221/2101* (2013.01)

(58) Field of Classification Search
CPC ............ G06F 21/6254; G06F 21/6245; G06F 21/6218; G06F 21/62; G06F 19/32;
(Continued)

(56) References Cited

U.S. PATENT DOCUMENTS 6,678,822 B1 * 1/2004 Morar ................ G06Q 10/0875
705/29
6,981,217 B1 12/2005 Knauft
(Continued)

FOREIGN PATENT DOCUMENTS

WO WO 2010-073214 7/2010
WO WO 2012-148817 11/2012

OTHER PUBLICATIONS

Pereira, "Distributional Clustering of English Words", Proceedings of Association for Computational Linguistics, 1993, pp. 183-190.
(Continued)

*Primary Examiner* — Zachary A. Davis
(74) *Attorney, Agent, or Firm* — Brian D. Bender

(57) ABSTRACT

At least some aspects of the present disclosure feature systems and methods for obfuscating data. The method includes the steps of receiving an input data stream including a sequence of n-grams, mapping at least some of the sequence of n-grams to corresponding dictionary terms using a dictionary, and disposing the corresponding tokens to an output data stream.

13 Claims, 10 Drawing Sheets

(58) Field of Classification Search
CPC ........ G06Q 50/24; G16H 10/00; G16H 10/60; G16H 50/70
See application file for complete search history.

(56) References Cited

U.S. PATENT DOCUMENTS

| | | | | |
|---|---|---|---|---|
| 7,158,979 | B2* | 1/2007 | Iverson | G06F 21/6254 |
| | | | | 707/741 |
| 7,269,548 | B2* | 9/2007 | Fux | G06F 17/2715 |
| | | | | 704/10 |
| 7,269,578 | B2 | 9/2007 | Sweeney | |
| 7,305,704 | B2* | 12/2007 | Ofek | H04L 47/10 |
| | | | | 713/168 |
| 7,376,677 | B2 | 5/2008 | Ober | |
| 7,519,591 | B2 | 4/2009 | Landi | |
| 7,668,820 | B2 | 2/2010 | Zuleba | |
| 7,711,542 | B2* | 5/2010 | Fux | G06F 17/289 |
| | | | | 341/22 |
| 7,712,029 | B2 | 5/2010 | Ferreira | |
| 7,801,720 | B2* | 9/2010 | Satake | G06F 17/289 |
| | | | | 704/2 |
| 7,823,207 | B2 | 10/2010 | Evenhaim | |
| 7,865,376 | B2 | 1/2011 | Ober | |
| 7,945,776 | B1* | 5/2011 | Atzmony | G06F 21/31 |
| | | | | 713/164 |
| 8,140,502 | B2 | 3/2012 | Francis | |
| 8,326,849 | B2 | 12/2012 | El Emam | |
| 8,725,714 | B2* | 5/2014 | Ai | G06F 21/6254 |
| | | | | 705/14.49 |
| 9,160,719 | B2* | 10/2015 | Marlow | H04L 63/0428 |
| 9,298,878 | B2* | 3/2016 | Guirguis | G06F 21/6254 |
| 9,323,892 | B1* | 4/2016 | Paris, III | G16H 10/40 |
| 10,235,377 | B2* | 3/2019 | Mueller | G06F 16/221 |
| 2002/0073099 | A1 | 6/2002 | Gilbert | |
| 2004/0249819 | A1* | 12/2004 | Matsumoto | G06F 17/2735 |
| 2008/0147554 | A1 | 6/2008 | Stevens | |
| 2008/0181396 | A1 | 7/2008 | Balakrishnan | |
| 2008/0118150 | A1 | 8/2008 | Balakrishnan | |
| 2008/0239365 | A1 | 10/2008 | Salgado | |
| 2009/0043817 | A1 | 2/2009 | Sanders | |
| 2010/0034376 | A1 | 2/2010 | Okuizumi | |
| 2010/0114840 | A1 | 5/2010 | Srivastava et al. | |
| 2011/0010563 | A1 | 1/2011 | Lee | |
| 2011/0077973 | A1 | 3/2011 | Breitenstein | |
| 2011/0225114 | A1 | 9/2011 | Gotthardt | |
| 2012/0030165 | A1 | 2/2012 | Guirguis et al. | |
| 2012/0078659 | A1 | 3/2012 | Ashrafzadeh | |
| 2012/0131075 | A1 | 5/2012 | Mawdsley et al. | |
| 2012/0266250 | A1 | 10/2012 | Uhl | |
| 2012/0278101 | A1 | 11/2012 | Homchowdhury | |
| 2012/0303616 | A1 | 11/2012 | Abuelsaad | |
| 2013/0297348 | A1 | 11/2013 | Cardoza | |
| 2014/0380445 | A1* | 12/2014 | Tunnell | G06F 21/00 |
| | | | | 726/7 |

OTHER PUBLICATIONS

Song, "Practical Techniques for Searches on Encrypted Data", Security and Privacy, IEEE Symposium, 2000, pp. 44-55.
"Clinical Research and The HIPAA Privacy Rule", U.S. Department of Health & Human Services, National Institutes of Health, Posted on Feb. 5, 2004, [retrieved from the internet on Jul. 4, 2016], URL <http://privacyruleandresearch.nih.gov/clin_research.asp>, pp. 1-16.
"Summary of the HIPAA Privacy Rule", U.S. Department of Health & Human Services, [retrieved from the internet on Jul. 4, 2016], URL <http://www.hhs.gov/ocr/privacy/hipaa/understanding/special/research/index.html>, pp. 1-25.
Kushida, "Strategies For De-Identification and Anonymization of Electronic Health Record Data For Use in Multicenter Research Studies", Stanford University Medical Center, 2012, pp. 1-23.
International Search report for PCT International application No. PCT/US2014/64741 dated Feb. 6, 2015, 2 pages.
Mulcahy, 10 Codes and Ciphers, Listverse, XP-002768789, Mar. 13, 2012, 3 pages.

* cited by examiner

SYSTEMS AND METHOD FOR OBFUSCATING DATA USING DICTIONARY

CROSS REFERENCE TO RELATED APPLICATIONS

This application is a national stage filing under 35 U.S.C. 371 of PCT/US2014/064741, filed Nov. 10, 2014, which claims the benefit of U.S. Provisional Application No. 61/904,223, filed Nov. 14, 2013, the disclosure of which is incorporated by reference in its entirety herein.

TECHNICAL FIELD

The present disclosure is related to obfuscating restricted, confidential, and private data where the obfuscated data can be used in research, investigation, and other data services.

SUMMARY

At least some aspects of the present disclosure feature a method for obfuscating data using a computer system having one or more processors and memories. The method includes the steps of: receiving a dictionary mapping a set of n-grams to dictionary terms; receiving a first data stream comprising a sequence of n-grams; comparing, by the one or more processors, each of the sequence of n-grams in the first data stream with the dictionary; and if the n-gram is in the dictionary, disposing a corresponding dictionary term in a second data stream.

At least some aspects of the present disclosure feature a system for obfuscating data implemented in a computer system having one or more processors and memories. The system includes a data retrieval module and a dictionary module. The data retrieval module is configured to retrieve a first data stream comprising a sequence of n-grams. The dictionary module is operative to look up each of the sequence of n-grams in the first data stream in a data dictionary, and if the n-gram is in the dictionary, to dispose a corresponding dictionary term in a second data stream.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

As the amount and type of personal and private data collected, stored, and analyzed continues to rise, governments all over the world have responded by enacting laws designed to protect individual privacy within this data. Privacy laws vary from country-to-country, but generally focus on upholding privacy of members through restricting access and dissemination of the data. Confidential information is also widely collected and used by large and small business and government organizations. At least some aspects of the present disclosure are directed to systems and methods for obfuscating private and/or confidential data while maintaining attributes allowing element or n-gram driven research and analysis of the obfuscated data. An element is a textual or numeric representation of data and may include a letter, a number, a word, a phrase, a sentence, an n-gram, or a paragraph. N-gram refers to a contiguous sequence of n words including numbers and symbols from a data stream, which typically is a phrase or a sequence of words with meaning. For example, "left leg" is a 2-gram, "bonfire" is a 1-gram, and "first thermal sensor" is a 3-gram. N-grams are generally interpreted to include any word, number (e.g., sequence of numbers as a single token in an n-gram), and/or symbol (usually symbols are stand-alone, like a comma or a period or a dollar sign as a single token in an n-gram). N-grams also typically include some "special" tokens such as "<start of sentence>" or such. In some cases, a data obfuscation system includes an obfuscation module to generate or apply mapping of an n-gram to a token. In some other cases, a data obfuscation system includes a dictionary module to use dictionary terms to replace n-grams and redact data to include only dictionary terms corresponding to the n-grams that are included in the dictionary.

At least some aspects of the present disclosure are directed to systems and methods that encrypt on an n-gram basis that is different from encrypting at a bit level. By tokenizing the n-gram and encrypting at that level, a data obfuscation system can perform data analysis on the tokenized n-grams without having the risk of exposing confidential and/or privacy data. For example, the system can apply machine learning algorithms on the encrypted or tokenized data. In some other cases, a data obfuscation system can tokenize elements in a document and perform data analysis on the tokenized elements.

Figure 1:
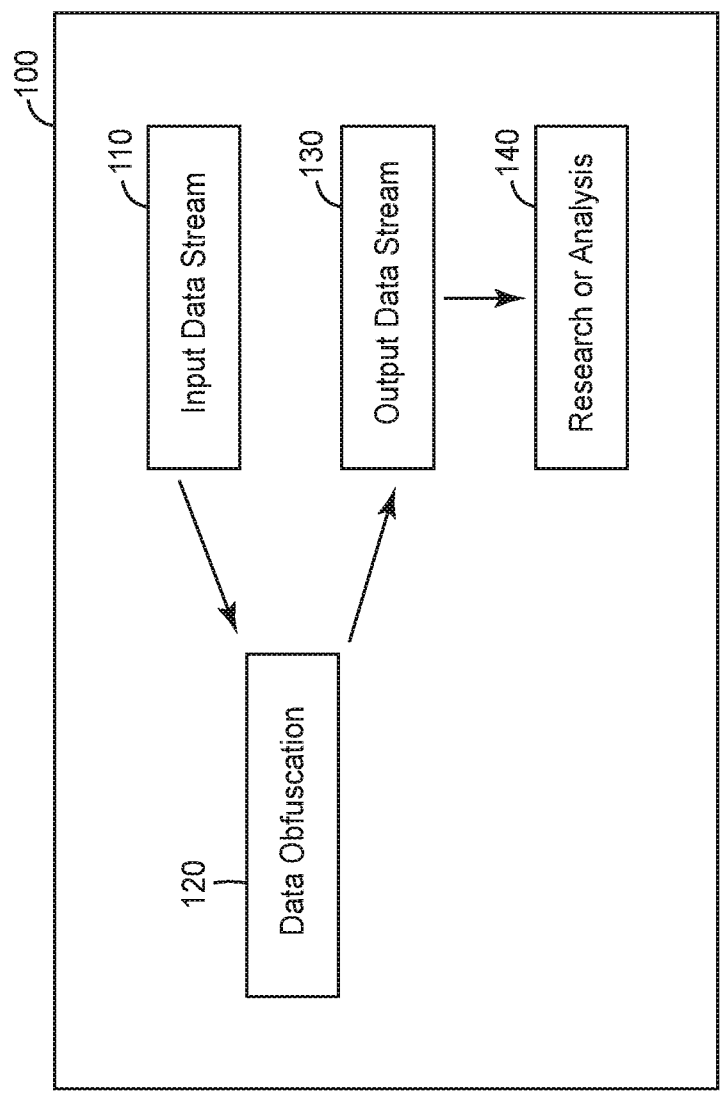
FIG. 1 illustrates a block diagram for an embodiment of a data obfuscation system.

FIG. 1 illustrates a block diagram for an embodiment of a data obfuscation system 100. The system 100 typically receives an input data stream 110, applies data obfuscation 120 to the input data stream 110 and generates an output data stream 130, and uses the output data stream 130 for further research or analysis 140.

In some cases, the input and output data stream can include content of or in the format of a document, a data set, a database record, data table, or the like. The data stream may contain sensitive data, for example, medical records, financial statements, technical specifications, legal contracts, academic publications, birth or death certificates, or the like. For example, medical records include but not limited to electronic health or medical records (EHR/EMR), physician notes, and billing or claim data.

Data obfuscation refers to methods of obfuscating data, mapping data and/or redacting data, for example, by eliminating private or personally identifiable data. At least some aspects of the present disclosure are directed to systems and methods for achieving data obfuscation. In a first embodiment, the data obfuscation 120 includes a one-to-one mapping in which every element of the input data stream 110 is mapped to an obfuscated token saved in the output data stream 130. In a second embodiment, the data obfuscation 120 includes an encryption method that maps a meaningful word into a new value that by itself has no meaning. In the first embodiment, the mapping retains the statistical properties of the input data stream 110 that, as an aggregate, can be valuable for identifying patterns without having to know the meaning behind the patterns thereby maintaining the confidentiality of the original data. The second embodiment does not maintain the one-to-one mapping. Instead, the data obfuscation 120 may map multiple words/phrases and even different sets of words to a single value. In this case, the obfuscation can be implemented because the mapping algorithm does not retain or store sensitive components of the original document.

In some embodiments, the data obfuscation 120 uses an obfuscation table to map an element or an n-gram to a token. In some cases, the obfuscation table maps variations of an element/n-gram to a token. A one-to-one mapping obfuscation method has the benefits that the statistics of the original text are maintained but the specific items (e.g, medical words, names, etc.) are obfuscated. In some cases, because the occurrence of sensitive data (e.g., protected health information) is not frequent when multiple documents are aggregated (i.e., the name of a person will not occur in many documents), most data analysis (e.g, machine learning algorithms) will naturally discount the sensitive data as a weak signal. However, those items that are good predictors (e.g., specific procedures or lab tests) will occur more frequently in an aggregated data stream (e.g., a combination of many medical documents). A token is used as a representation of an element or an n-gram, for example, the token may be a decimal value, hexadecimal value, alphanumeric string, or the like. In some other embodiments, the data obfuscation 120 uses a predefined data dictionary to perform a first level summarization of a data set before the element/n-gram obfuscation is performed.

In some embodiments, the system 100 or another computer system receives the output data stream and applies a statistical process on the second data stream generating a statistical result. Application of a statistical process provides valuable insight and information about underlying patterns and knowledge that exist within the data. In addition to statistical processing, other classification and computational techniques can be performed including: machine learning, regression, data mining, visualization, or the like. For example, a user may want to know if there are items within medical documentation that predicts a Potentially Preventable Condition (PPC) such as sepsis. Potentially Preventable Conditions (PPC) are negative events or outcomes that result from the process of medical care or treatment. One machine learning approach that can make use of elements, specifically n-grams, within this context is using a clustering algorithm that uses the n-grams as the feature vector for a particular document (Pereira et al. "Distributional Clustering of English Words" Association for Computational Linguistics (ACL '93), pp 183-190, 1993). In this case, a user may want to cluster documents that are generated from similar types of diagnosis and procedures. By using the n-grams within the documents, a user can build a high-dimensional representation and based on the words used (or tokens used in this case) the user can find documents of similar type.

Often following the identification of hidden structure in data (e.g., unsupervised clustering), it is useful to understand what features are used to define class inclusion versus exclusion. This can be valuable to better understand aspects of the data that are difficult to interpret without aggregating the data. For example, it might be found that the unsupervised classifier inadvertently created two classes (based on the text) for a single n-gram (e.g., appendicitis). By looking at the features that created the class exclusion, one might find that these two classes are used differently in the original data stream (e.g., two different procedures). However, in order to be able to determine this, a user would want to go from the obfuscated data back to the original data. In some cases, a user could utilize the obfuscation table to determine the original data that is mapped to the obfuscated data. Another approach is to use a random seed that is used to encrypt and tokenize the original data and then provide the random seed to the user to "decode" or "unmap" the obfuscation when needed and/or under the appropriately controlled situation. This could be done with a look-up table or simply inverting the encryption technique using the originally generated encryption key.

Many data (e.g., medical records, legal records, etc.) contain both structured data (i.e., fields that take specific values with explicitly stated labels such as "Age") and unstructured data (i.e., free written text generated by the caretaker). Typically the structured data is a subset of the information that is available in the unstructured text and because of this, it has been shown that there can be more predictive power when one uses the unstructured data than when one uses the structured data to generate predictive or patient classification models. It is frequently the case that structured data is incorrect, out of date, or lacks critical details that are more accurately captured in the unstructured data (e.g., clinical summary, etc.). For example, in healthcare data, a lot of life-style issues are being used in predictive modeling (alcohol use, smoking, living alone, etc.) which are not structured elements (e.g., an actual diagnosis of alcohol abuse). As another example, to classify documents in which there were occurrences of PPC versus those in which there were not, a user can identify the word(s) in the unstructured text that are better to differentiate the two groups of documents. Utilizing the obfuscated tokens, a user would be able to safely work with the data (with the same statistics of the original text) to determine if there are text elements that best predict a PPC. Once it is determined that there is an appropriate signal, a user could determine the words or features that can better classify the documents. Furthermore, this classification can lead to signals or features that can predict PPCs.

Figure 2:
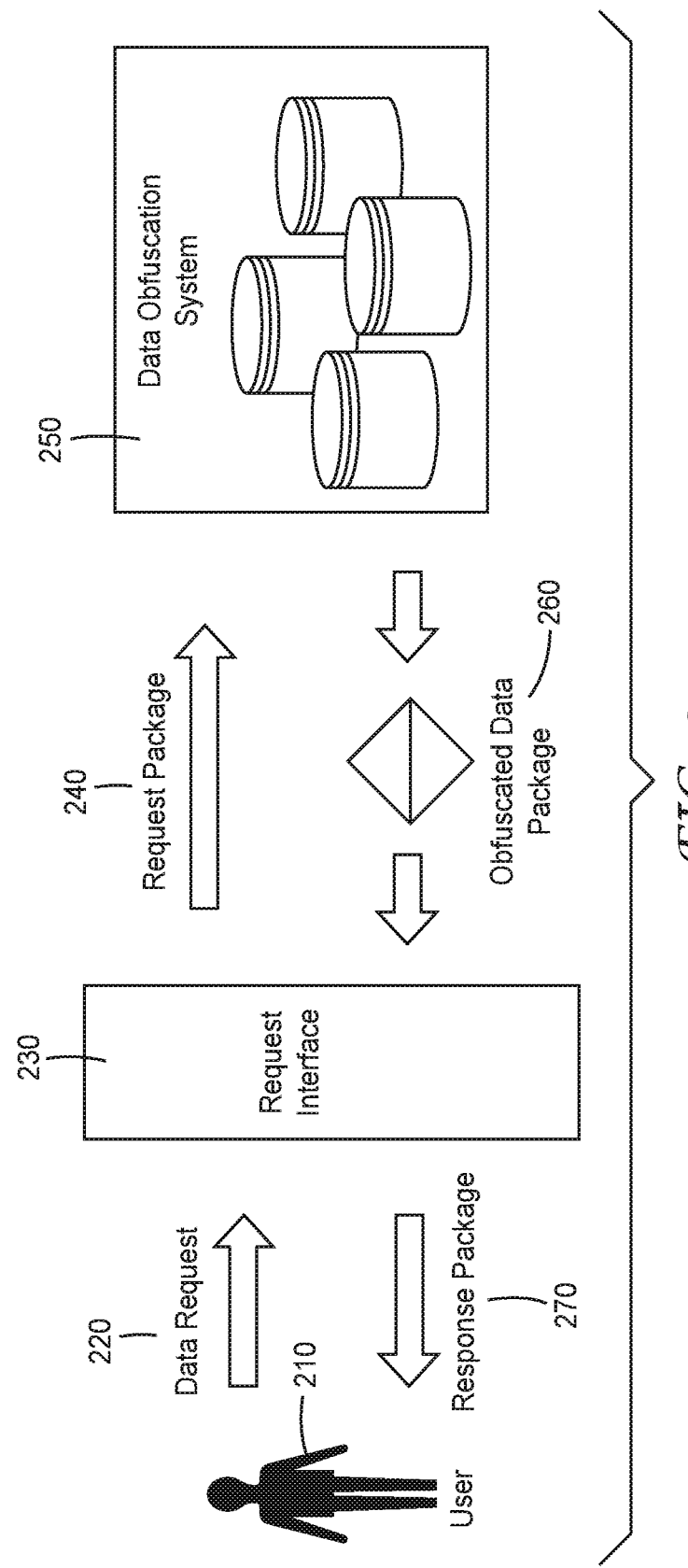
FIG. 2 illustrates a data flow diagram for an embodiment of providing data service using a data obfuscation system.

FIG. 2 illustrates a data flow diagram for an embodiment of providing data service using a data obfuscation system. First, a user (e.g., a researcher) 210 sends a data request 220 to retrieve data from the system. In one embodiment, the data request 220 includes the data being requested, the type of package this data will be delivered within, and the user credentials of the user 210. The data being requested describes the specific fields and sets of data desired by the user. The data package type describes the structure of the data once it has been processed to obfuscate or remove the private or restricted information. An optional parameter of the data request 220 includes the user credentials. The credentials are used by the system to enforce access control, log use of data and maintain other compliance and regulatory requirements. Next, the request interface 230 receives the data request 220 and composes a request package 240 that is either equivalent to the data request 220 or includes additional information such as user credentials to the data obfuscation system 250. The data obfuscation system 250 receives the request package 240 and optionally validates the user credentials. The data obfuscation system 250 retrieves data according to request, and obfuscates and/or redacts data according to the data request and/or the data type. The data obfuscation system 250 compiles an obfuscated data package 260 and a response package 270 is transmitted via the request interface 230. The user 210 can perform further research activities on the data contained in the response package 270.

Figure 3A:
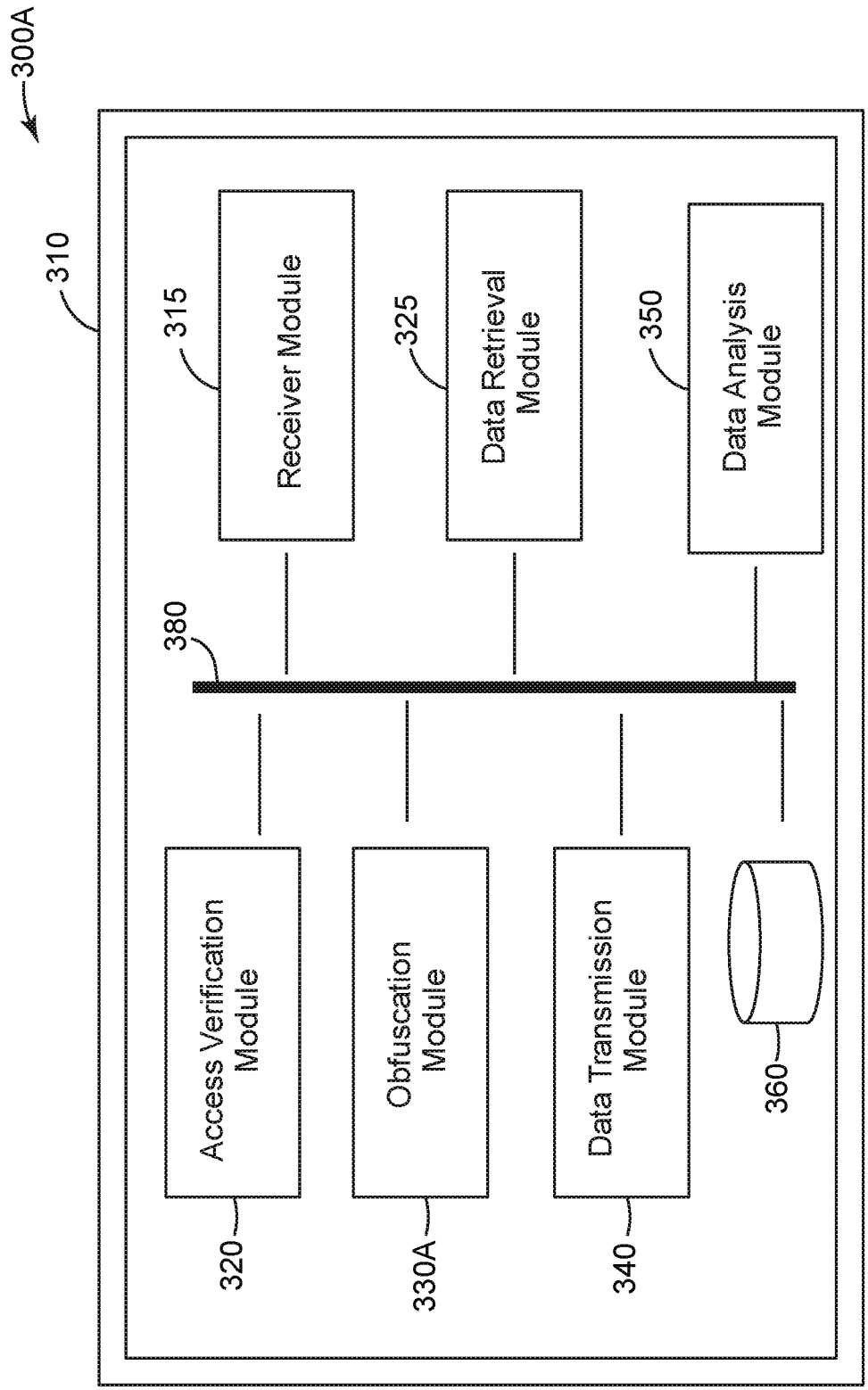
FIG. 3A is a module diagram illustrating an embodiment of a data obfuscation system.

FIG. 3A is a module diagram illustrating an embodiment of a data obfuscation system 300A. The system 300A includes a receiver module 315, an access verification module 320, a data retrieval module 325, an obfuscation module 330A, a data transmission module 340, a data analysis module 350, data repository 360, and communication interface 380. One or more modules illustrated in FIG. 3A are optional, such as the access verification module 320, and/or the data analysis module 350. In some embodiments, the data obfuscation system 300A can be implemented on a computer system 310 including one or more processors and memories.

Various components of the data obfuscation system 300A can be implemented by one or more computing devices, including but not limited to, circuits, a computer, a processor, a processing unit, a microprocessor, and/or a tablet computer. In some cases, various components of the data obfuscation system 300A can be implemented on a shared computing device. Alternatively, a component of the system 300A can be implemented on multiple computing devices. In some implementations, various modules and components of the system 300A can be implemented as software, hardware, firmware, or a combination thereof. In some cases, various components of the data obfuscation system 300A can be implemented in software or firmware executed by a computing device.

The receiver module 315 is configured to receive a request for data. The request can be submitted from a HTTP request, an API call, a database query, or the like. As an example, the user opens a website that contains a list of data that is viewable based upon their authorization access level. User authorization access level may be a numeric designation (e.g., Level 1, 2, etc) or indicated by a status such as restricted or unrestricted. Numeric designation may be system defined. As an example, Level 1 access may permit visibility to all the data contained within a document. Within the receiver module 315, the user selects data with possible constraints (e.g., data field, date ranges, location, etc). For example, a user would like to analyze medical records that were updated for a population of patients treated for appendicitis during the first quarter of 2013. The user enters a Jan. 1, 2013 to Mar. 31, 2013 date range in the date field and selects a medical condition related to the appendix in a condition field on the receiver module 315.

The access verification module 320 may verify user credentials, for example, whether the login information is correct, whether the user is authorized to request data, whether the rights granted to the user allow the user to make the specific request. The access verification module 320 can also direct the obfuscation module 330A about the potential obfuscation methods available to a particular user. For example, one user may be allowed to request data in a raw n-gram format, where another user may only be allowed to request data after it has been passed through a predefined data dictionary.

The data retrieval module 325 retrieves a first data stream in response to the request received. The first data stream typically includes a sequence of n-grams. The first data stream is provided to the obfuscation module 330A. In one embodiment, the obfuscation module 330A can generate a second data stream; for each of the n-grams, use a obfuscation table to identify a corresponding token; dispose the corresponding token in the second data stream. In some cases, the obfuscation table is generated for one or more data streams retrieved. In some other cases, the obfuscation table is stored in a data repository and can be retrieved when it is needed.

In some embodiments, the type of data requested by the researcher defines the operations on the data that will be performed before the private information has been processed and deemed safe for viewing and use by the researcher. The type and definition of possible data packages varies by application and restrictions or legislation applicable to the application data. For example, a type of data is Protected Health Information (PHI) data.

In one embodiment, the obfuscation module 330A is configured to extract the n-grams (e.g., words and phrases, etc.) from a data stream and perform a one-way obfuscation (e.g. one-way hash) routine on each n-gram. Many methods exist in current literature describing how to extract individual n-grams from a data stream. One of the simplest methods is to split the n-grams using a predefined delimiter character. In the case of a textual data stream, the most common delimiter character is a space. Other delimiters include, but are not limited to, other forms of punctuation, key words or phrases, and document section headers or titles. In addition to extraction of individual words, methods exist to formulate element or n-gram objects from individual words. The process of generating element or n-gram sequences in a data stream is known in literature and implemented in many existing systems. Once all the n-grams have been extracted, tokens can be generated using the obfuscation table to an obfuscated output data stream.

Tokens can be generated in many ways, including random number generation, alphanumeric seeding and consecutive index counting. The study of methods to generate random numbers is one that has been evaluated for several decades, culminating in the development of a variety of methods for generating random sequences. Once a random number has been generated, it can be used in its native form as the token, or utilized as a seed to generate the token in a different representation. A token can be represented as a number, a hexadecimal number, an alphanumeric representation, binary string, textual representation, or the like. This technique will obfuscate private and confidential information, while still maintaining word occurrence and position information contained from the original data. This type of technique is optimal for statistical based research methods that rely little on the actual content of the data, but look for usage or occurrence patterns in a dataset. In some cases, a consistent one-way obfuscation scheme is utilized across all documents within a data request to maintain consistency and statistical properties across the dataset. In some implementations, the obfuscation module 330A generates the obfuscation table by creating a mapping for an n-gram when the n-gram is first encountered in the first data stream.

The data transmission module 340 is configured to compile a response package using the data stream provided by the obfuscation module 330A and transmit the response package. In some cases, the response package can include at least part of, or some translated form of, the obfuscation table. In some cases, the conversion of obfuscated tokens back into original data format can be critical to the data analytics process and the interpretation of statistical assessment results. For example, a researcher performing analysis on a set of medical documents may discover that an obfuscated token (e.g., 0x83223CCA) precedes a token (e.g., 0x11355340) in 93% of document occurrences. In the event of this discovery, the researcher would submit a request to the proposed system for original document text for tokens (e.g., 0x83223CCA) and (e.g., 0x11355340). In this example, the researcher could have discovered that a particular behavior, consuming antacids (e.g., 0x83223CCA), always precedes a diagnosis, appendicitis (e.g., 0x11355340).

The data analysis module 350 provides the functions and processes to conduct the statistical analysis and data processing functions necessary to derive valuable knowledge and information from the obfuscated output data stream. In addition to statistical processing, other classification and computational techniques can be performed including: machine learning, regression, data mining, visualization, or the like. For example, a user may want to know if there are items within medical documentation that predict a Potentially Preventable Condition (PPC) such as sepsis. Potentially Preventable Conditions (PPC) are negative events or outcomes that results from the process of medical care or treatment. One machine learning approach that can make use of elements, specifically n-grams, within this context is using a clustering algorithm that uses the n-grams as the feature vector for a particular document. In this case, a user clusters documents that are generated from similar feature vector or types of diagnosis and procedures. By using the n-grams within the documents, a user builds a high-dimensional representation and based on the words used (or tokens used in this case) the user can find documents of similar type.

The data repository 360 may include any transitory and non-transitory computer readable medium to store information and data for the data obfuscation system 300A, including but not limited to, privacy and/or confidential data, requests, user credentials, data dictionaries, obfuscation maps, and response data packages. The data repository 360 may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository 360, for example, may be a single relational database such as SQL Server from Microsoft Corporation. In some cases, the data repository 360 may include a plurality of databases that can exchange and aggregate data by data integration process or software application. In an exemplary embodiment, at least part of the data repository 360 may be hosted in a cloud data center.

Various components of the system 300A can communicate via or be coupled to via a communication interface 380, for example, a wired or wireless interface. The communication interface includes, but is not limited to, any wired or wireless short-range and long-range communication interfaces. The short-range communication interfaces may be, for example, local area network (LAN), interfaces conforming to a known communications standard, such as Bluetooth® standard, IEEE 802 standards (e.g., IEEE 802.11), a ZigBee® or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet.

Figure 4A:
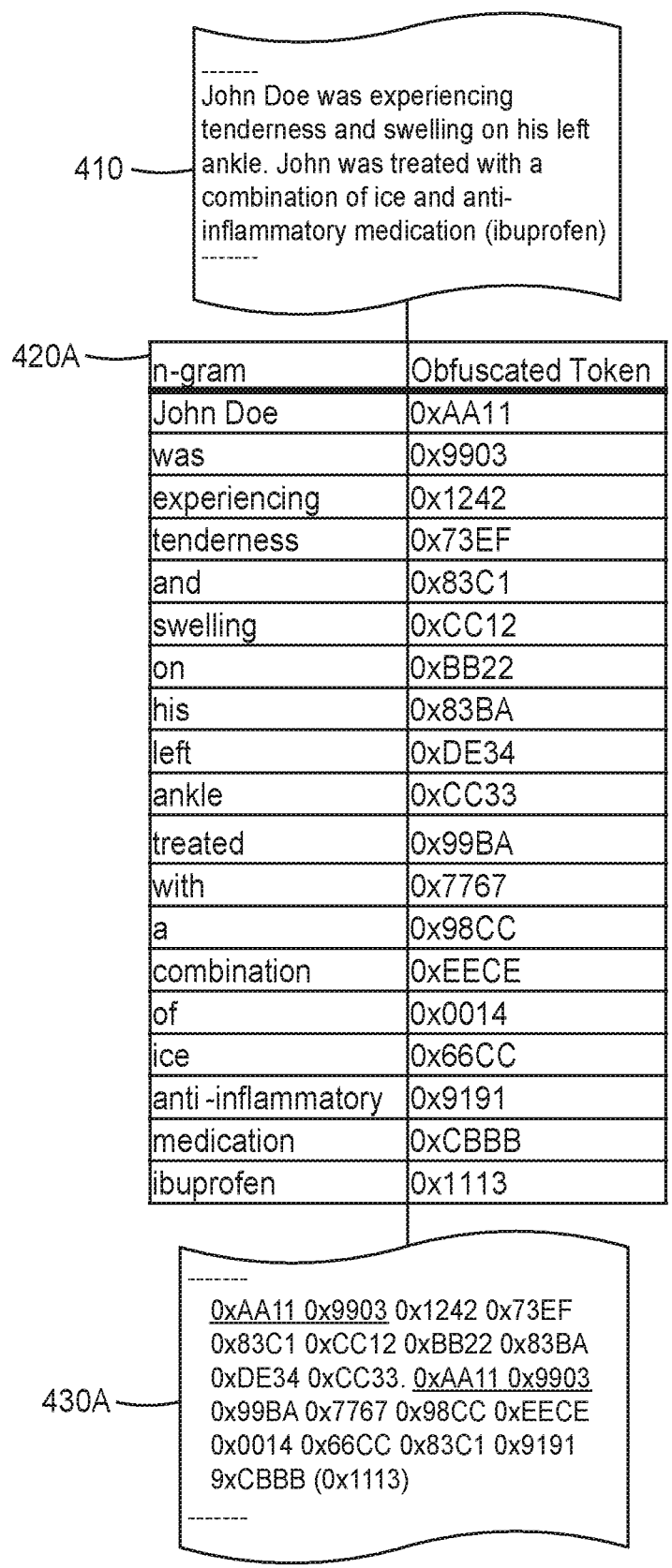
FIGS. 4A and 4B show examples of the process and output format of data obfuscation using an obfuscation table.

An example of the process and output format of data obfuscation is shown below in FIG. 4A. A first data stream 410 containing private and/or confidential data is retrieved. An obfuscation table 420A is used to tokenize the first data stream 410 and generate a second data stream 430A. In some cases, the first data stream 410 is retrieved according to a data request. In some cases, a set of data streams including the first data stream 410 are retrieved according to a data request. In some other cases, the first data stream 410 is retrieved according to an on-going data request, for example, clinic visit summaries for a certain type of disease. In some implementations, the obfuscation table 420A is created based on the n-grams in the first data stream 410. In some other implementations, the obfuscation table 420A is created based on n-grams in a set of data streams. In some cases, the obfuscation table 420A is continuously revised and updated based on data streams retrieved.

Figure 4B:
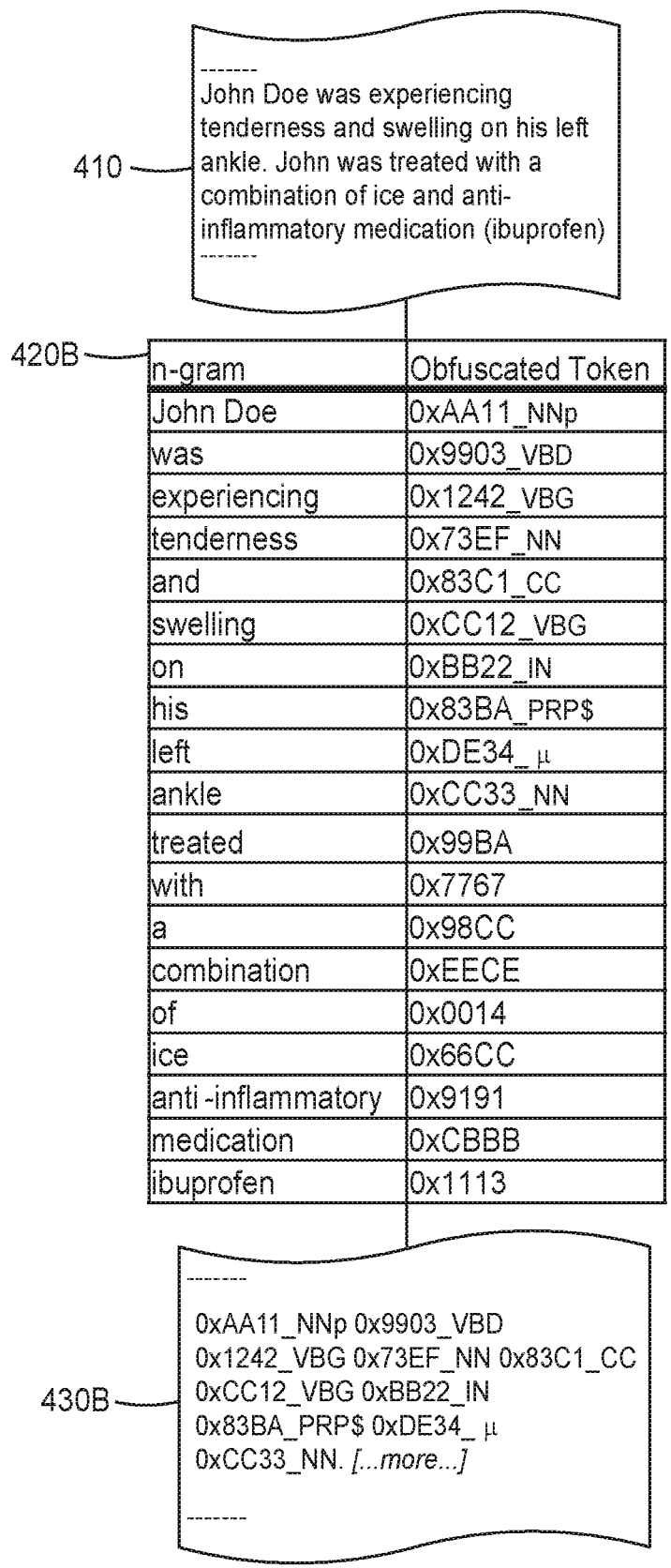

In some cases, research to be conducted relies on the underlying structure of a document, for example, parts of speech. The obfuscation table and/or the tokens can include such information. For example, an additional field can be appended onto the end of each token to encode this information, as illustrated in FIG. 4B. In the example described in FIG. 4B, each obfuscated token in the obfuscation table 420B has been appended with a part-of-speech identifier. As an example, the original name (John Doe) has been obfuscated through the data package process, but the structure of the word within the sentence has been maintained by appending the NNP (noun, proper, singular) tag to the end of the obfuscated token. Using the obfuscation table 420B, a second data stream 430B is generated.

Figure 3B:
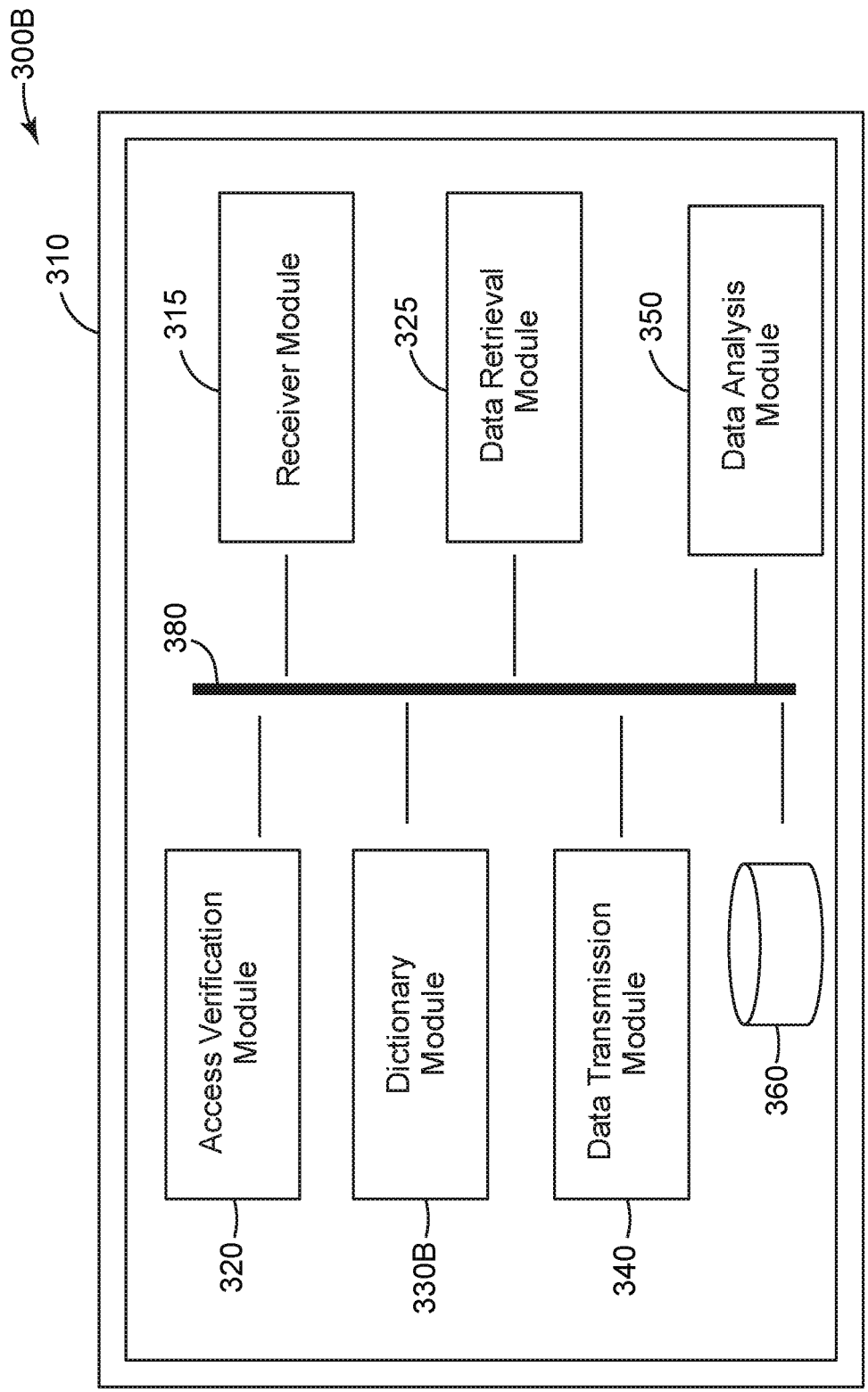
FIG. 3B illustrates a module diagram of an embodiment of a data obfuscation system using the data dictionary approach.

In some embodiments, a data dictionary approach can be used to protect privacy and confidential data. For example, any restricted data can be removed and only words or phrases listed in the data dictionary can be mapped to standardized dictionary terms and provided to a user for further research and analysis. FIG. 3B illustrates a module diagram of an embodiment of a data obfuscation system 300B using the data dictionary approach. The system 300B includes a number of modules that are the same as the data obfuscation system 300A illustrated in FIG. 3A, including the receiver module 315, the access verification module 320, the data retrieval module 325, the data transmission module 340, the data analysis module 350, the data repository 360, and the communication interface 380. The system 300B includes a dictionary module 330B to perform data obfuscation and masking. One or more modules illustrated in FIG. 3B are optional, such as the access verification module 320, and/or the data analysis module 350. In some embodiments, the data obfuscation system 300B can be implemented on a computer system 310 including one or more processors and memories. Processors may each comprise a general-purpose microprocessor, a specially designed processor, an application specific integrated circuit (ASIC), a field programmable gate array (FPGA), a collection of discrete logic, or any type of processing device capable of executing the techniques described herein. In one example, memory may store program instructions (e.g., software instructions) that are executed by one or more processors to carry out the techniques described herein. In other examples, the techniques may be executed by specifically programmed circuitry of a processor. In these or other ways, processor may be configured to execute the techniques described herein.

Various components of the data obfuscation system 300B can be implemented by one or more computing devices, including but not limited to, circuits, a computer, a processor, a processing unit, a microprocessor, and/or a tablet computer. In some cases, various components of the data obfuscation system 300B can be implemented on a shared computing device. Alternatively, a component of the system 300B can be implemented on multiple computing devices.

In some implementations, various modules and components of the system 300B can be implemented as software, hardware, firmware, or a combination thereof. In some cases, various components of the data obfuscation system 300B can be implemented in software or firmware executed by a computing device.

In some cases, the dictionary module 330B maps a set of n-grams to dictionary terms to perform data obfuscation. The dictionary terms can be, for example, standardized terminology (e.g., joint, contract, etc.), tokens, or symbols (e.g., a134m, c343, etc.) representing the standardized term. In such cases, the dictionary module 330B receives a first data stream retrieved by the data retrieval module 325. The first data stream includes a sequence of n-grams. The dictionary module 330B generates a second data stream and compares each of the sequence of n-grams in the first data stream with the dictionary. If the n-gram is included the dictionary, the dictionary module 330B disposes a dictionary term corresponding to the n-gram in the second data stream; and if the n-gram is not included in the dictionary, the dictionary module 330B will evaluate the next n-gram.

Figure 5A:
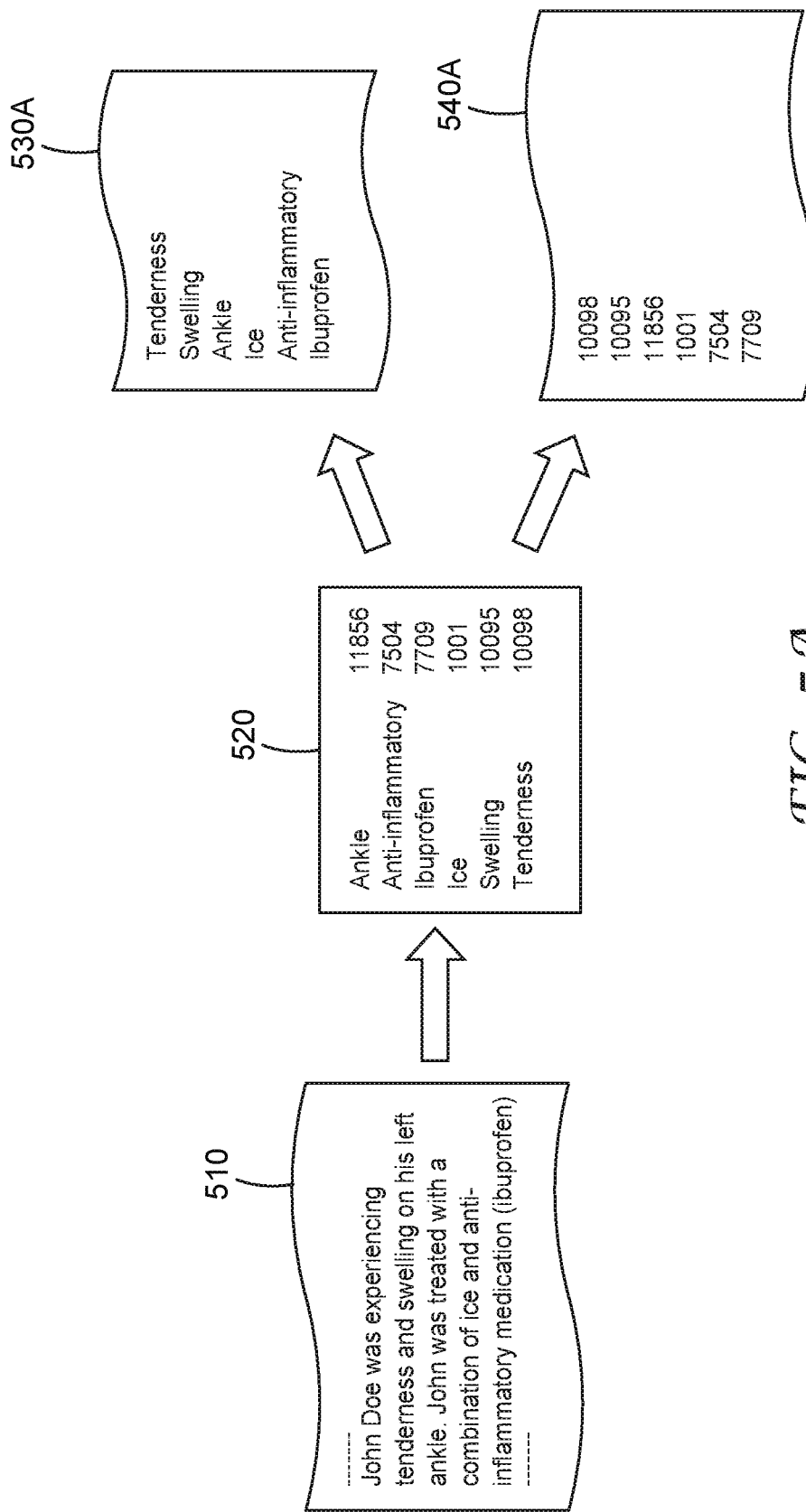
FIGS. 5A and 5B show examples of the process and output format of data obfuscation using a data dictionary.

The data dictionary approach can be tailored to research involving key words and phrases associated with a dataset. The process involved in producing this data package takes a raw data document and parses it to identify key words or phrases from a predefined data dictionary, for example, a 3M™ Health Data Dictionary (HDD). These words and phrases listed in the predefined data dictionary have been identified as key information to use in the related domains. The output of this data package type is a list of textual or numeric terms or values (e.g., Numeric Concept Identifier (NCID)) from the data dictionary that have occurred or within the requested dataset. An example of the process and output format of this data package are shown below in FIG. 5A. A first data stream 510 containing private and/or confidential data is retrieved. A data dictionary 520 is used to provide dictionary look-up and mapping to generate a second data stream 530A, which contains terms (i.e., standardized terms, etc.) that are listed in the dictionary. In an alternative embodiment, the system may generate a second data stream 540A, which contains tokens representing the dictionary terms, after the dictionary look-up and mapping. In some cases, the first data stream 510 is retrieved according to a data request. In some cases, a set of data streams including the first data stream 510 are retrieved according to a data request. In some other cases, the first data stream 510 is retrieved according to an on-going data request, for example, clinic visit summaries for a certain type of disease. In some implementations, the dictionary module redacts the first data stream to include n-grams that are listed in the data dictionary 520 to the second data stream. In some other implementations, the dictionary module maps various n-grams in the first data stream 510 to dictionary terms in textual format and disposes the dictionary terms in the second data stream 530A or the dictionary terms in token format in the second data stream 540A.

Figure 5B:
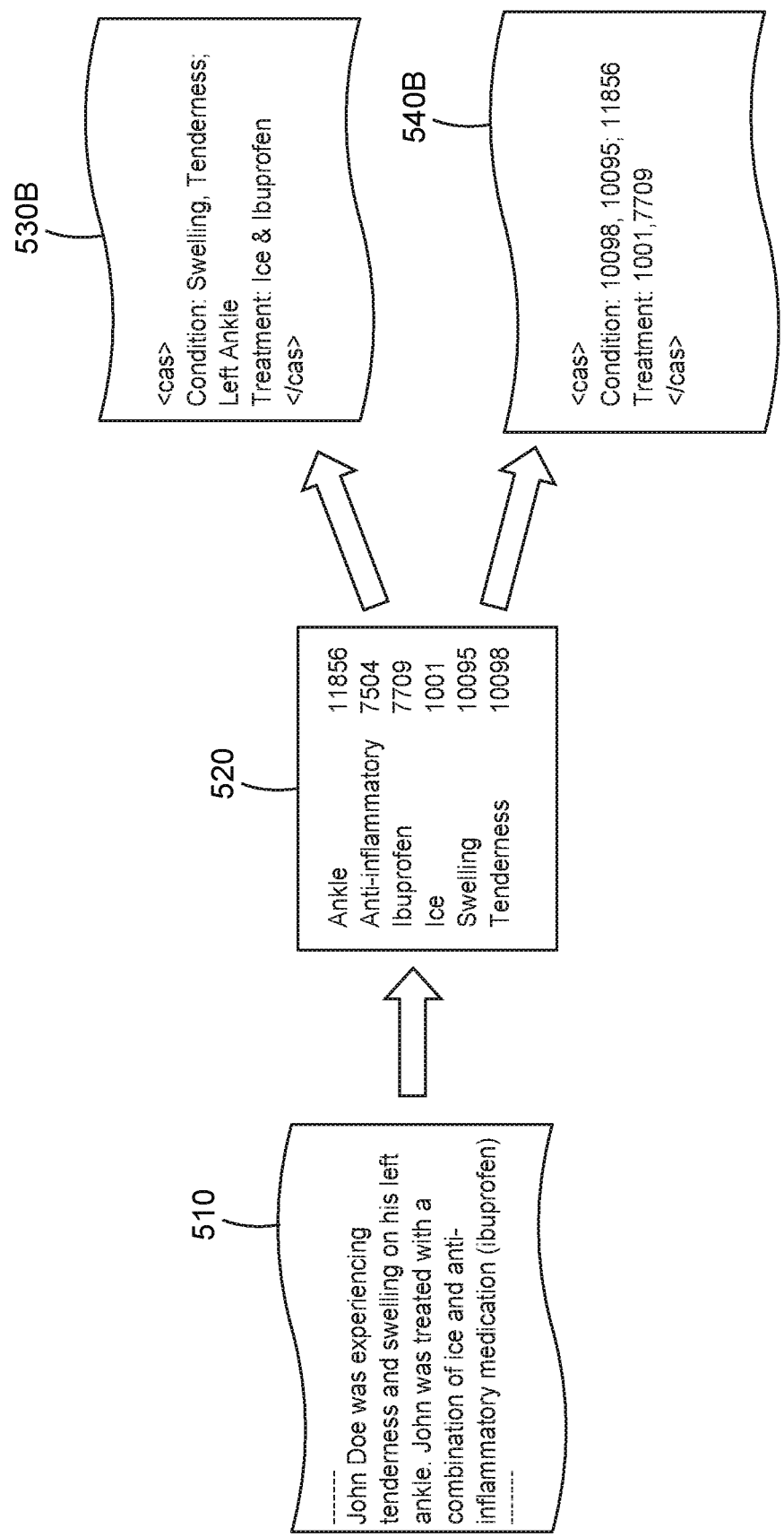

In some embodiments, the dictionary module uses a specific output format for the second data stream, as illustrated in FIG. 5B. For example, a Common Annotation Structure (CAS) can be used. The CAS summarizes the contents of the data stream into a standard format using consistent language and nomenclature. Once data has been processed into the CAS format, as illustrated as 530B containing dictionary terms in textual format and 540B containing dictionary terms in token format, it can easily be consumed by automated processing techniques.

Figure 6A:
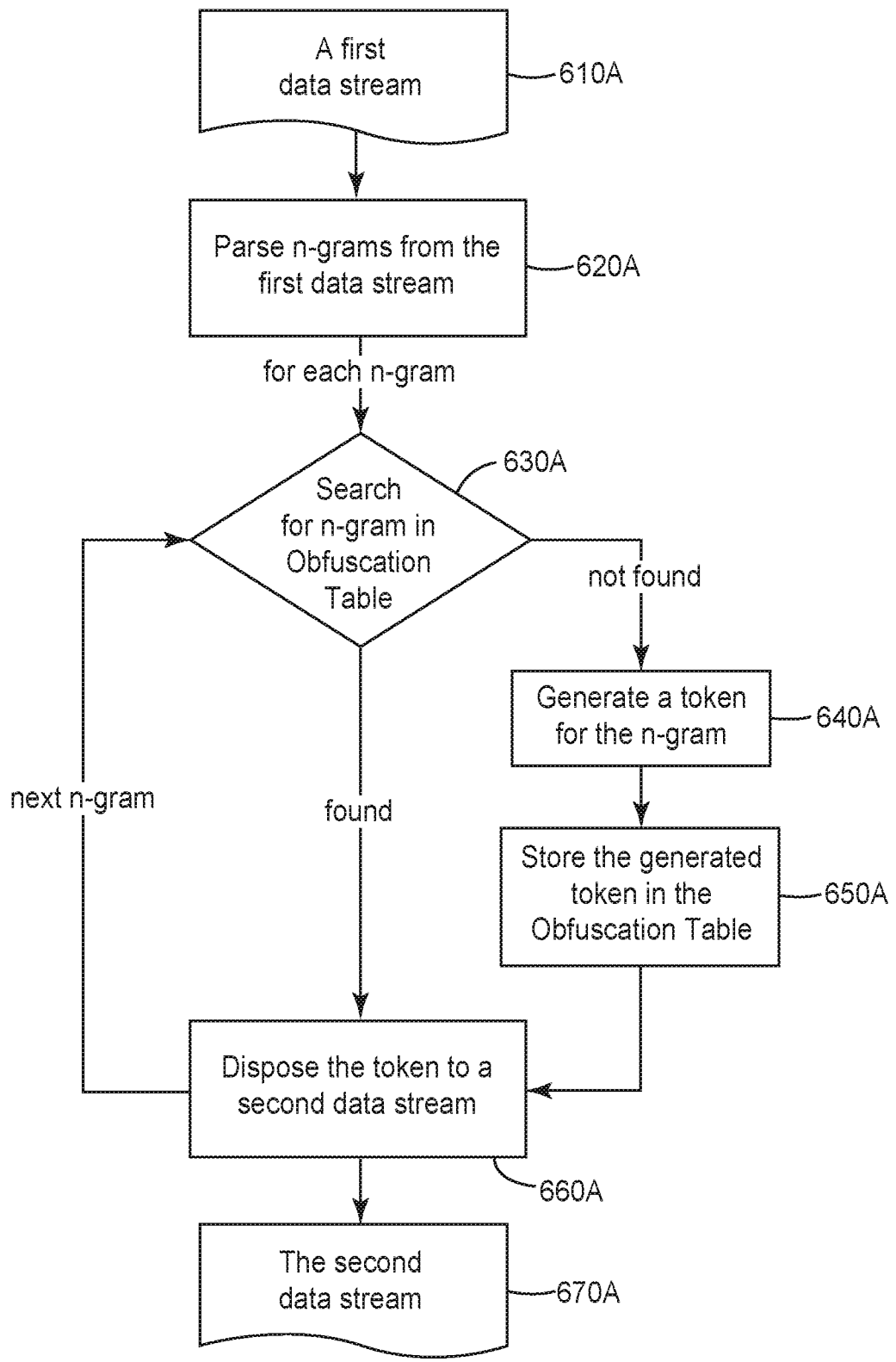
FIGS. 6A and 6B illustrate functional flow diagrams for embodiments of a data obfuscation system.
Figure 6B:
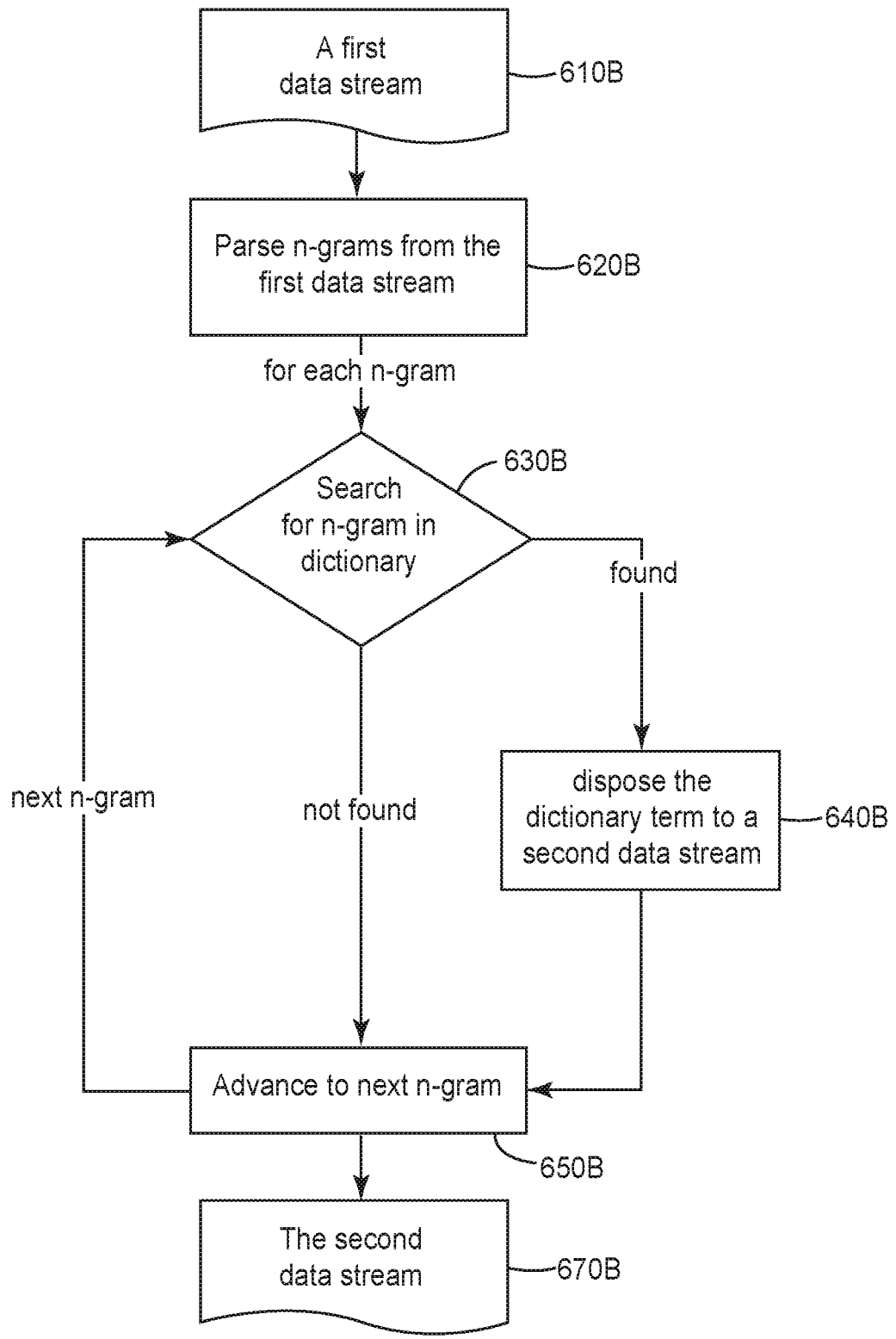

FIG. 6A illustrates a functional flow diagram for an embodiment of a data obfuscation system. First, the system receives a first data stream (step 610A), for example, a document. The first data stream includes a sequence of n-grams. Next, the system parses the n-grams from the first data stream (step 620A). In some cases, the system may separate the first data stream into individual elements (e.g., words) and then group the individual elements into n-grams. For each n-gram, the system searches for the n-gram in the obfuscation table (step 630A). If the n-gram is in the obfuscation table, the system disposes the corresponding token identified from the obfuscation table in a second data stream (step 660A). In some cases, the corresponding token comprises a metadata describing the properties of the n-gram. If the n-gram is not in the obfuscation table, the system generates a token for the n-gram (step 640A); stores the generated token in the obfuscation table (step 650A); and disposes the token in the second data stream (step 660A). In some cases, each of the n-grams has a position in the sequence in the first data stream, and the corresponding token is disposed at the same position in the second data stream as the position of the n-gram. After each n-gram in the first data stream is processed, the second data stream is provided either in a data transmission package or for further research and analysis (step 670A).

First, the system receives a first data stream (step 610B), for example, a data set. The first data stream includes a sequence of n-grams. Next, the system parses the n-grams from the first data stream (step 620B). For each n-gram, the system searches the n-gram in the dictionary (step 630B). If the n-gram is in the dictionary, the system disposes the corresponding dictionary term in a second data stream (step 640B). In some cases, the dictionary term can be identical to the n-gram. In some other cases, the dictionary term can map to a number of n-grams having similar meanings. If the n-gram is not in the dictionary, the system advances to the next n-gram (step 650B). In some cases, each of the n-grams has a position in the sequence in the first data stream, and the corresponding dictionary term is disposed at the same relative position in the second data stream as the position of the n-gram. After each n-gram in the first data stream is processed, the second data stream is provided either in a data transmission package or for further research and analysis (step 670B).

In some embodiments, the second data stream comprises a predetermined data structure including descriptors (e.g., condition, treatment, fee, etc.). In such embodiments, the system will dispose the dictionary terms along with the descriptors. The descriptors may be metadata describing the categories, functions, units, or other information regarding the n-grams, for example. As another example, "abdominal tenderness" is contained with a document, the assigned dictionary term would become 1009896 and may be assigned a 'diagnosis' descriptor (e.g., x100) by the system.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

Exemplary Embodiments

Embodiment 1. A method for obfuscating data using a computer system having one or more processors and memories, comprising:

receiving a dictionary mapping a set of n-grams to dictionary terms;

receiving a first data stream comprising a sequence of n-grams;

comparing, by the one or more processors, each of the sequence of n-grams in the first data stream with the dictionary; and if the n-gram is in the dictionary, disposing a corresponding dictionary term in a second data stream.

Embodiment 2. The method of Embodiment 1, wherein the second data stream comprises a predetermined data structure including one or more descriptors.

Embodiment 3. The method of Embodiment 2, wherein at least one of the one or more descriptors describes a category of dictionary terms.

Embodiment 4. The method of any one of Embodiment 1 through Embodiment 3, wherein the corresponding dictionary term is identical to the n-gram.

Embodiment 5. The method of any one of Embodiment 1 through Embodiment 4, wherein the corresponding dictionary term is a token representing the n-gram.

Embodiment 6. The method of any one of Embodiment 1 through Embodiment 5, further comprising:

applying, by the one or more processors, a statistical process on the second data stream.

Embodiment 7. The method of Embodiment 6, wherein the statistical process comprises n-gram-based statistical analysis that generates an n-gram based statistics.

Embodiment 8. The method of any one of Embodiment 1 through Embodiment 7, wherein the first or second data stream comprises at least one of a document, a data set, a database record, and a medical record.

Embodiment 9. The method of Embodiment 7, further comprising:

interpreting the n-gram based statistics using the dictionary.

Embodiment 10. The method of Embodiment 6, further comprising:

predicting a relationship of a combination of n-grams with an event.

Embodiment 11. The method of Embodiment 10, wherein the event is predetermined.

Embodiment 12. A system for obfuscating data implemented in a computer system having one or more processors and memories, comprising:

a data retrieval module configured to retrieve a first data stream comprising a sequence of n-grams;

a dictionary module operative to:

look up each of the sequence of n-grams in the first data stream in a data dictionary; and if the n-gram is in the dictionary, disposing a corresponding dictionary term in a second data stream.

Embodiment 13. The system of Embodiment 12, wherein the second data stream comprises a predetermined data structure including one or more descriptors.

Embodiment 14. The system of Embodiment 13, wherein at least one of the one or more descriptors describes a category of dictionary terms.

Embodiment 15. The system of any one of Embodiment 12 through Embodiment 14, wherein the corresponding dictionary term is identical to the n-gram.

Embodiment 16. The system of any one of Embodiment 12 through Embodiment 15, wherein the corresponding dictionary term is a token representing the n-gram.

Embodiment 17. The system of any one of Embodiment 12 through Embodiment 16, further comprising:

a receiver module configured to receive a request for data from a user, wherein the data retrieval module retrieve the first data stream according to the request for data.

Embodiment 18. The system of Embodiment 17, further comprising:

an access verification module configured to receive user information entered by the user and verify access level of the user.

Embodiment 19. The system of any one of Embodiment 12 through Embodiment 18, further comprising:

a data transmission module coupled to the dictionary module and configured to compile a response package using the second data stream.

Embodiment 20. The system of Embodiment 19, wherein the data transmission module is further configured to compile the response package to include at least part of the dictionary.

Embodiment 21. The system of any one of Embodiment 12 through Embodiment 20, further comprising:

a data analysis module configured to receive the second data stream and apply a statistical process to the second data stream.

Embodiment 22. The system of Embodiment 21, wherein the data analysis module is further configured to generate an n-gram-based statistics using the statistical process.

Embodiment 23. The system of any one of Embodiment 12 through Embodiment 22, wherein the first or second data stream comprises at least one of a document, a data set, a database record, and a medical record.

Embodiment 24. The system of Embodiment 21, wherein the data analysis module is further configured to predict a relationship of a combination of n-grams with an event.

Embodiment 25. The system of Embodiment 24, wherein the event is predetermined.

What is claimed is:

1. A method for obfuscating data using a computer system having one or more processors and memories, the method comprising:

obtaining, by the one or more processors, a dictionary that includes a set of predefined dictionary terms and a set of n-grams and that maps the set of n-grams to the predefined dictionary terms;

receiving, by the one or more processors, a first digital data stream comprising a sequence of n-grams, wherein each respective n-gram represents either a respective single word or a respective contiguous sequence of words, wherein 'n' represents a number of words in the respective contiguous sequence, and wherein the first data stream is from multiple documents;

parsing, by the one or more processors, the first data stream to distinguish each respective n-gram of the sequence of n-grams received in the first data stream;

comparing, by the one or more processors, each respective n-gram of the sequence of n-grams received in the first data stream with the predefined dictionary terms included in the dictionary;

when a respective n-gram is identified in the dictionary based on the comparing, disposing, by the one or more processors, a corresponding dictionary term in a second digital data stream, wherein the second data stream comprises a predetermined data structure including one or more descriptors, wherein the corresponding dictionary term is an obfuscated token representing the respective n-gram, wherein the obfuscated token comprises a part-of-speech identifier that is appended to the obfuscated token, and after each n-gram in the first data stream has been compared, the second data stream comprises only a plurality of obfuscated tokens;

applying, by the one or more processors, a statistical process on the second data stream, wherein the statistical process includes at least determining one or more usage patterns of one or more of the obfuscated tokens in the second data stream;

generating, by the one or more processors, one or more feature vectors based on the second data stream;

providing, by the one or more processors, the one or more feature vectors to a machine learning model having been trained to perform a clustering analysis on any number of received feature vectors;

performing, by the one or more processors and using the machine learning model, the clustering analysis of the one or more feature vectors;

identifying, by the one or more processors, documents based on the results of the clustering analysis; and predicting, by the one or more processors and using the identified documents, one or more potentially preventable conditions.

2. The method of claim 1, wherein at least one of the one or more descriptors describes a category of dictionary terms.

3. The method of claim 1, further comprising:
predicting, by the one or more processors, a relationship between the one or more potentially preventable conditions and a combination of n-grams from the subset of n-grams disposed in the second data stream.

4. The method of claim 1, further comprising:
encrypting and tokenizing, by the one or more processors, the first data stream using a random seed; and
providing, by the one or more processors, the random seed to the user to reverse the obfuscation of one or more obfuscated tokens in the second data stream.

5. The method of claim 1, wherein n is greater than 1.

6. The method of claim 1, further comprising:
applying, by the one or more processors, one or more machine learning algorithms on the one or more determined usage patterns associated with the obfuscated tokens of the second data stream.

7. A computer system comprising:
a memory storing a dictionary that maps a set of n-grams to predefined dictionary terms; and
one or more processors in communication with the memory, the one or more processors being configured to:
  obtain the dictionary from the memory;
  receive a first digital data stream comprising a sequence of n-grams, wherein each respective n-gram represents either a respective single word or a respective contiguous sequence of words, wherein 'n' represents a number of words in the respective contiguous sequence, and wherein the first data stream is from multiple documents;
  parse the first data stream to distinguish each respective n-gram of the sequence of n-grams received in the first data stream;
  compare each respective n-gram of the sequence of n-grams received in the first data stream with the predefined dictionary terms included in the dictionary;
  when a respective n-gram is identified in the dictionary based on the comparing, dispose a corresponding dictionary term in a second digital data stream, wherein the second data stream comprises a predetermined data structure including one or more descriptors, wherein the corresponding dictionary term is an obfuscated token representing the respective n-gram, wherein the obfuscated token comprises a part-of-speech identifier that is appended to the obfuscated token, and after each n-gram in the first data stream has been compared, the second data stream comprises only a plurality of obfuscated tokens;
  apply a statistical process on the second data stream, wherein the statistical process includes at least determining one or more usage patterns of one or more of the obfuscated tokens in the second data stream;
  generate one or more feature vectors based on the second data stream;
  provide the one or more feature vectors to a machine learning model having been trained to perform a clustering analysis on provided feature vectors;
  perform, using the machine learning model, the clustering analysis of the one or more feature vectors;
  identify documents based on the results of the clustering analysis; and
  predict, using the identified documents, one or more potentially preventable conditions.

8. The system of claim 7, wherein the one or more processors are further configured to:
receive a request for data from a user,
wherein to receive the first data stream, the one or more processors are configured to retrieve the first data stream from the memory in response to receipt of the request for data received from the user.

9. The system of claim 7, wherein the one or more processors are further configured to generate one or more n-gram-based statistics using the statistical process.

10. The system of claim 7, wherein at least one of the first data stream or the second data stream comprises at least one of a document, a data set, a database record, or a medical record.

11. The system of claim 7, wherein the one or more processors are further configured to predict a relationship between the one or more potentially preventable conditions and a combination of n-grams from the subset of n-grams disposed in the second data stream.

12. The system of claim 7, wherein the one or more processors are further configured to:
encrypt and tokenize the first data stream using a random seed; and
provide the random seed to the user to reverse the obfuscation of one or more obfuscated tokens in the second data stream.

13. The system of claim 7, wherein the one or more processors are further configured to apply one or more machine learning algorithms on the one or more determined usage patterns associated with the obfuscated tokens in the second data stream.

* * * * *